United States Patent [19]

Beaulieu et al.

[11] Patent Number: 5,030,556

[45] Date of Patent: Jul. 9, 1991

[54] SPECIES-SPECIFIC DNA PROBE FOR THE DETECTION OF BRANHAMELLA CATARRHALIS

[76] Inventors: Danielle Beaulieu, 3297 rue l'Heureux, Apt. 1, Ste-Foy, Quebec; Paul H. Roy, 28, Charles Garnier, Loretteville, Quebec; Michel G. Bergeron, 2069 Brulart, Sillery, Quebec, all of Canada

[21] Appl. No.: 330,448

[22] Filed: Mar. 30, 1989

[51] Int. Cl.$^5$ .......................... C12Q 1/00; C12Q 1/68
[52] U.S. Cl. ........................................ 435/6; 435/4; 435/29; 436/94; 436/501
[58] Field of Search ................ 435/6, 4, 29; 436/501, 436/94; 935/77, 78

[56] References Cited

U.S. PATENT DOCUMENTS 4,358,535 11/1982 Folkow et al. .......................... 435/6

OTHER PUBLICATIONS

Beaulieu, D. et al., "Characterization, Use of as a Molecular Probe...", Abstr. Annu. Meet. Am. Soc. Microbiol, vol. 87(0), p. 149 (1987).

Beaulieu, D. et al., "Characterization of a Plasmid from..." Plasmid, vol. 20, pp. 158-162 (1988).

Knapp, "Historical Perspectives and Identification of Neisseria and Related Species", Oct. 1988, vol. I, No. 4, pp. 415-431.

CA 221758w—Rossau et al.

CA 12543h—Van Embden et al.

Primary Examiner—Robert A. Wax
Assistant Examiner—Eric Steffe
Attorney, Agent, or Firm—Cushman, Darby & Cushman

[57] ABSTRACT

There is provided by the present invention, a method for detecting the presence of *Branhamella catarrhalis*, said method comprising; depositing and fixing on an inert support a sample containing DNA fragments in substantially single stranded form, contacting said fixed single stranded genetic material with a labelled probe consisting of a fragment of *B. catarrhalis* chromosomal DNA, identified as ATCC 53879, being capable of hybridizing with *B. catarrhalis* DNA in the sample, said contacting being under hybridizing conditions at a predetermined stringency; and detecting duplex formation on said support by means of said label.

2 Claims, 1 Drawing Sheet

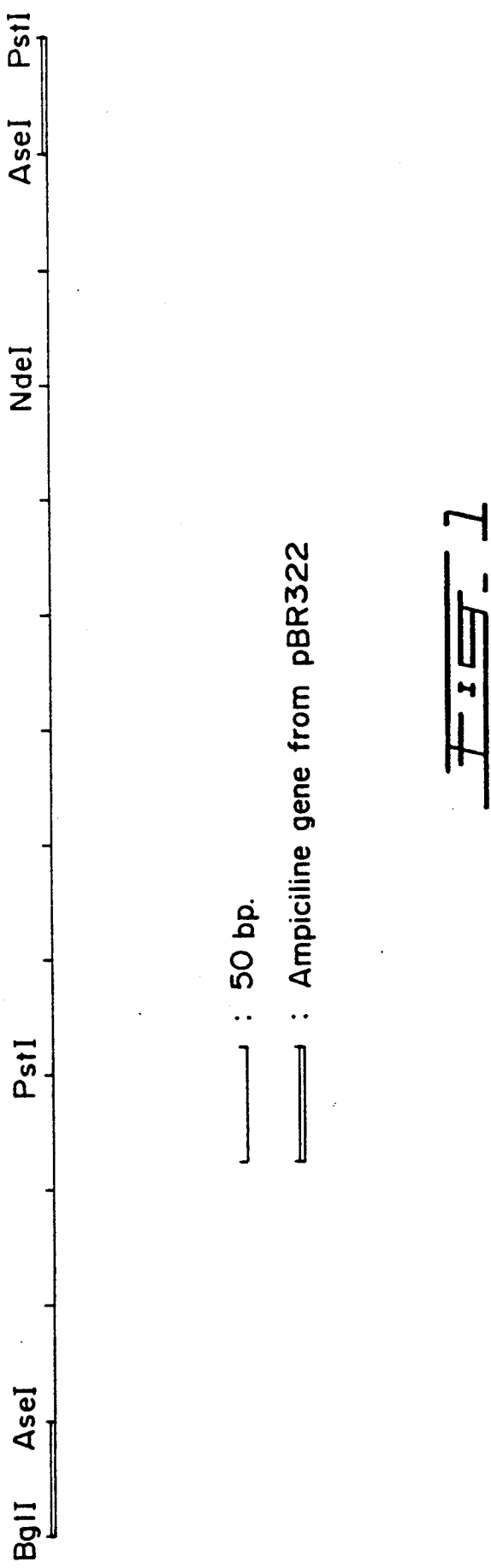

5,030,556

SPECIES-SPECIFIC DNA PROBE FOR THE DETECTION OF *BRANHAMELLA CATARRHALIS*

BACKGROUND OF THE INVENTION

*Branhamella catarrhalis* belongs to the Neisseriaceae family and a gram stain will reveal a gram negative diplococcus much like those typical for any Neisseria species. It is an aerobic microorganism that is part of the normal human microflora of the nasopharynx. The carrier rate is lower in adults than in children, and nowadays, acute otitis media caused by *B. catarrhalis* is often found in children. *B. catarrhalis* is a new pathogen; in 1977, it acquired a new resistance gene capable of inactivating ampicillin. Since then, the percentage of resistant strains isolated in hospitals is increasing steadily and is becoming a problem. Before the 1980's, there was no concern for the correct identification of *B. catarrhalis* in the microbiology laboratory since it was considered harmless, but since then this microorganism's pathogenic potential has been increasing. Now, many researchers are concerned that clinical laboratories, especially smaller laboratories can not or do not identify *B. catarrhalis* properly.

Presently, identification of *B. catarrhalis* in these laboratories is done either by standard biochemical methods, which require at least 48 to 72 hours of incubation time, or by rapid identification tests made for Neisseria and related species. In any case, the clinical sample must first be cultivated and purified since all of these tests require a pure culture as inoculum. Both methods have their advantages and disadvantages. As it was described by Knapp (Microbiological Reviews, vol 1, no. 4, p. 415-431, (1988)), the traditional tests have the advantage that they provide a more detailed characterization of isolates. Unfortunately, they have the major disadvantage that their use may delay the identification of an isolate unnecessarily. In contrast, some rapid tests may not always provide an accurate identification because they give limited information about an isolate.

As far as *Branhamella catarrhalis* is concerned, identification by standard biochemical methods is time consuming while use of the rapid tests can be inaccurate. Also noticed by Knapp (mentioned above), the species that are the most difficult to distinguish from *N. gonorrhoeae* by biochemical characteristics are *N. cinerea, B. catarrhalis* and *K. denitrificans.*

There are certain biochemical reactions such as the production of acid from glucose and maltose, reduction of nitrate, superoxol production, and colistin susceptibility that can differentiate these species, but some or all of these reactions yield the same results for many Neisseria species and for *B. catarrhalis*. The only biochemical test that separates *B. catarrhalis* from the other Neisseria species is the production of an extra-cellular DNase; for which *B. catarrhalis* tests positive while the others are negative. Although this DNase test can differentiate *B. catarrhalis* from other Neisseria, it takes at least 72 hours of incubation time before the plates can be read.

In the last 3 or 4 years, rapid identification kits specific for certain genera of bacteria have appeared on the market. Such kits exist for Neisseria and related species. Their major advantage is that most of the common reactions used in standard biochemical identification can all be done at once and in less time. The kits that are presently on the market for Neisseria and related species can be separated into two categories: acid production tests and enzyme substrate tests. A pattern of acid production from a variety of sugars cannot, by itself, provide an identification for *B. catarrhalis* so enzyme substrate tests have to be used. These tests are based on the observation of the color change of a solution of a chromogenic substrate into which the strain is inoculated. The enzymes tested include: β-galactosidase, γ-glutamylaminopeptidase and hydroxypropylaminopeptidase. Since *B. catarrhalis* does not produce any of these enzymes, the strain tested is presumptively identified if none of the enzymes are produced by the test isolate (Knapp, J. S., mentioned above). Some kits on the market combine acid production tests and enzyme production tests and these kits provide a better identification of most species. However, these would not be any better for *B. catarrhalis* since neither of these tests provides a direct identification. Also, only gram-negative, oxidase-positive diplococcal isolates should be inoculated in the tests.

As Knapp stated, the products that incorporate enzyme substrate tests alone must be used according to the limitations of the manufacturer; that is, only strains isolated on selective media should be confirmed in these tests.

Many studies have been done to check the precision of these and other tests for the identification of *B. catarrhalis* strains. Most of the time, the more popular tests correctly identified 95 to 100% of the Neisseria and related species, but *B. catarrhalis* identification was always presumptive.

The use of any of these kits or of the standard biochemical methods requires prior purification of the strain from the clinical specimen. Moreover, for the rapid test kits, some preliminary tests such as oxidase production and gram stain have to be performed so that only selected strains are processed with the kits, otherwise, the results might be faulty.

It would be highly desirable if there could be provided a probe specific to *Branhamella catarrhalis*, which could be used as an identification tool in the clinical microbiology laboratory.

Further, it would also be greatly appreciated if there could be a faster, more reliable, and more direct test for *B. catarrhalis* available on the market.

Ultimately, it would be a great improvement if there could be a test for *B. catarrhalis* which requires no purification step.

SUMMARY OF THE INVENTION

Surprisingly and in accordance with the present invention, there is provided a specific DNA probe to *Branhamella catarrhalis* which renders possible its identification in a very short period of time.

Since our probe is specific to *Branhamella catarrhalis*, it can be used as an identification tool in the clinical microbiology laboratory. Our species-specific DNA probe would eliminate all the problems and disadvantages encountered with the methods in current use. It would greatly reduce the time presently required to identify *B. catarrhalis* in the clinical laboratory since it could be used directly on clinical specimens with only a short pretreatment of the specimen to allow the release of bacterial DNA. In addition to being 100% specific, this probe provides a reliable, direct identification of the species, either in mixed or pure cultures.

Furthermore, since no purification of the sample is required by using this specific probe, the presence or absence of *B. catarrhalis* is confirmed in a very short time, usually the same day the sample arrives at the laboratory.

IN THE DRAWINGS

FIG. 1 shows the restriction map of the 550 bp. *B. catarrhalis* chromosomal DNA insert.

DETAILED DESCRIPTION OF THE INVENTION

A small fragment of chromosomal DNA which is used as a species-specific probe to detect in vitro the presence of this microorganism has been isolated from a clinical strain of *Branhamella catarrhalis*, deposited as ATCC 53879,. The fragment has no known function in the genome, that is, it does not belong to a particular gene, and it is 400 base pairs (bp) in length.

The probe was constructed in the following manner:

First isolated were numerous small restriction fragments, approximately 500 to 800 bp, of *B. catarrhalis* chromosomal DNA which were to be tested for specific hybridization to *B. catarrhalis* DNA, and which were then to be shortened to the size of approximately 100 bp or to a 30–50 base oligonucleotide. A differential hybridization experiment was done using the closest taxonomic relatives of *B. catarrhalis* to isolate this fragment since this method had proved to be successful for the construction of probes for other species (Abstracts ASM no Q53, 1988). Differential hybridization consists in Southern transferring total digests of the chromosomal DNA of the probe organism (in our case *B. catarrhalis* ATCC 53879 DNA) and of its closest relative to a nylon membrane and then hybridizing that membrane with labeled chromosomal DNA of the probe organism. Usually a second blot, identical to the first, is hybridized concomitantly with labeled chromosomal DNA of the relative. The two blots are then compared with each other and a region of fragments of *B. catarrhalis* DNA is identified where no probe hybridized on either blot. That way, we reduce the chances of randomly taking a fragment that would cross-hybridize with the relative. *Neisseria elongata* is the closest relative of *B. catarrhalis* when strains from human origin only are considered. These two species have approximately 6% chromosomal homology between them (Henriksen, S. D. (1976). Ann Rev Microbiol. 30:63–83.). A prior attempt for the construction of a probe for *B. catarrhalis* was made and cross-hybridization problems were observed with some *Haemophilus influenzae* strains, so it was decided to include a strain of *H. influenzae*, along with the strain of *N. elongata* in the differential hybridization experiment. In order to generate the small fragments, the restriction enzyme to be chosen had to degrade the DNA to short fragments. Several enzymes were tried without success because the three bacteria did not have the same G+C content; *B. catarrhalis* has 40% G+C, *H. influenzae* has 39% G+C and *N. elongata* has >55% G+C. This situation made it impossible to get all three chromosomal DNAs properly degraded. To resolve this situation, the differential hybridization was done between *H. influenzae* and *B. catarrhalis* only. Since these two bacteria had low G+C contents, we chose a restriction enzyme that recognized an AT rich sequence so that there would be a high frequency of sites in the chromosomal DNAs thus generating small fragments. The restriction endonuclease chosen was AseI; this enzyme recognizes a 6 bp sequence composed uniquely of ATs and has a single site in the ampicillin resistance gene of pBR322 thus providing us with a suitable cloning vector.

The differential hybridization experiment was conducted as described above and the probe used was *B. catarrhalis* ATCC 53879 $^{32}$P labeled chromosomal DNA. Since there is very little homology between the chromosomal DNAs of *B. catarrhalis* and *H. influenzae*, it was felt that the second blot was not needed; the chances of using a fragment that would cross-hybridize with *H. influenzae* were already very small. After autoradiography, a region from 400 to 2000 bp AseI fragments was identified in the chromosomal DNA of *B. catarrhalis* ATCC 53879 DNA, where the DNA of *H. influenzae* showed no homology to the probe. Any of these could possibly yield a species specific probe; therefore, different fragments from this region were purified and cloned into dephosphorylated pBR322. Mini-preparations of plasmid DNA were done with the first 17 clones obtained from a mixture of fragments from 400 to 700 bp. These mini-preparations were subsequently Southern transferred and hybridized to a *B. catarrhalis* chromosomal DNA probe to select the strongest clones for trial as species specific probes. Of the 17 clones, 2 did not have an insert, 1 had an unexpected length and bizarre migration pattern, 4 were weak, 3 were intermediate and the remaining 7 were strong. Three of these 7 were selected randomly to be assayed as species probes against several species of Neisseria and Moraxella and clone number 2 was found to be specific.

This clone 2 had an insert of 550 bp in length and we found it contained 2 restriction sites: one PstI site and one NdeI site (FIG. 1). The PstI site divided the insert into two fragments of 400 and 150 bp each. When assayed as probes, both fragments retained the specificity displayed by the total insert. We later found that the 400 bp fragment was more specific than the 150 bp so our probe is 400 bp in length. We intend to sequence this fragment and then derive an oligonucleotide probe from the sequence.

Here is the list of strains against which the probe was first tested: 1 *Moraxella lacunata*, 3 *Moraxella nonliquefaciens*, 1 *Moraxella osloensis*, 1 *Moraxella phenylpyruvica*, 2 *Moraxella urethralis*, 1 *Neisseria cinerea*, 2 *Neisseria elongata*, 1 *Neisseria flavescens*, 1 *Neisseria gonorrhoeae*, 1 *Neisseria lactamica*, 1 *Neisseria meningitidis*, 2 *Neisseria mucosa*, 2 *Neisseria sicca*, 1 *Neisseria subflava*, 1 *Neisseria ovis*, 1 *Neisseria caviae*, 1 *Neisseria cuniculi*, 2 *Haemophilus influenzae*, 2 *Escherichia coli*.

This 400 bp chromosomal DNA fragment is currently labeled with the radioactive nucleotide α-$^{32}$P(dATP) which is incorporated into the DNA fragment by a Random Primer labeling reaction (non-radioactive labeled nucleotides such as biotin labeled nucleotides can also be incorporated into the DNA by this method). This is an enzymatic reaction which requires a single stranded DNA template and produces a double stranded DNA molecule which has one strand labeled and the other (the template) unlabeled. This DNA molecule then has to be denatured to yield the final product, a radioactive single stranded DNA molecule, the probe, which can then be hybridized to any single stranded target DNA fixed on a solid support or in solution. The target DNA is whole cell DNA from different genera of bacteria found in clinical samples or inoculated from pure cultures. This DNA is either irreversibly fixed on a nylon membrane or other solid support or free in solution, after its release from the bacterium and its denaturation. Since the target DNA is now single stranded, it is free to hybridize to the probe. The conditions under which the hybridization and post-hybridization washes take place are dependent on the degree of stringency desired; for this 400 bp probe, the conditions used are the following: pre-hybridization solution: 50% formamide, 5×SSC (1×SSC=0.15M NaCl, 0.015M NaCitrate), 0.1% SDS (Sodium Dodecyl Sulfate), 1× Denhardt (50× Denhardt=1% BSA, 1% Ficoll, 1% Polyvinylpyrrolidone), 75 mg/ml single stranded DNA (Salmon Sperm DNA), 50° C., 3 to 4 hours. Hybridization solution: fresh prehybridization solution containing the labeled probe, 42° C., overnight. Post-hybridization washes: 0.1× to 1×SSC, 0.1% SDS, 68° C. for 1 hour with shaking at 50 RPM (New-Brunswich incubator/-shaker). These conditions are generally considered to be very stringent, the most critical factor being the salt concentration in which the post-hybridization washes take place.

Once the filters or solid supports have been washed free of all loose labeled probe, the detection of the hybridized probe can be done either by autoradiography, by scintillation counting, or by adding a series of substrates which produce a visible color where the probe is hybridized. Of course the detection method used depends on the label used. If there is any homology between the probe and the target DNA, the probe will still be linked to the target DNA on the support and therefore will emit radioactivity which will be recorded by the X-Ray film or the counter, or will produce a visible color.

To complete the specificity tests of the probe, we tested one species to represent each genus of bacteria that can be found in the human healthy or non-healthy respiratory tract, except for the Neisseriaceae family and the Haemophilus genus where we tested 5 strains of each species (when 5 were available). Here is the list of the strains tested against both fragment probes: NEISSERIACEAE family: 5 Acinetobacter calcoaceticus lwoffi, 5 Acinetobacter calcoaceticus anitratus, 63 Branhamella catarrhalis, 3 Kingella denitrificans, 2 Kingella indologenes, 2 Moraxella atlantae, 2 Moraxella lacunata, 5 Moraxella nonliquefaciens, 5 Moraxella osloensis, 2 Moraxella phenylpyruvica, 4 Moraxella urethralis, 3 Neisseria cinerea 2 Neisseria elongata, 4 Neisseria flavescens, 5 Neisseria gonorrhoeae, 2 Neisseria lactamica, 5 Neisseria meningitidis, 3 Neisseria mucosa, 1 Neissera polysaccharea, 5 Neisseria sicca, 2 Neisseria subflava, 2 Neisseria subflava (flava), 1 Neisseria subflava (perflava); ANIMAL STRAINS: 1 Neisseria ovis, 1 Neisseria caviae, 1 Neisseria cuniculi, 1 Neisseria animalis, 1 Neisseria canis; HAEMOPHILUS SPP: 5 Haemophilus influenzae, 5 Haemophilus parainfluenzae, 5 Haemophilus haemolyticus, 5 Haemophilus parahaemolyticus, 2 Haemophilus aphrophilus, 5 Haemophilus paraphrophilus, 5 Haemophilus segnis, AEROBIC, GRAM +: 1 Corynebacterium xerosis, 1 Micrococus lysodeikticus, 1 Staphylococcus aureus, 1 Streptococcus pneumoniae, 1 Streptococcus viridans, 1 Streptococcus salivarius, 1 Streptococcus ∂-hemolytic, 1 Streptococcus β-hemolytic, AEROBIC, GRAM —: 1 Enterobacter cloacae, A Escherichia coli, 1 Klebsiella pneumoniae, 1 Proteus mirabilis, 1 Pseudomonas aeruginosa, 1 Pseudomonas putida, 1 Salmonella spp (group B), 1 Serratia marcescens, 1 Shigella spp, ANAEROBIC, GRAM +: 1 Actinomyces israelii, 1 Eubacterium limosum, 1 Lactobacillus spp, 1 Peptostreptococcus assacharolyticus, 1 Propionibacterium acnes, ANAEROBIC, GRAM —: 1 Bacteroides fragilis, 1 Bacteroides melaninogenicus, 1 Fusobacterium nucleatum, 1 Veillonella parvula.

The results of these hybridizations are listed in Table 1.

TABLE 1

RESULTS OF HYBRIDIZATION EXPERIMENTS

| MICRO-ORGANISM | No STRAINS TESTED | PROBE TEST METHOD | No STRAINS THAT HYBRIDIZE WITH | | |
|---|---|---|---|---|---|
| | | | 550 BP | 150 BP | 400 BP |
| NEISSERIACEAE | | | | | |
| Acinetobacter calcoaceticus lwoffi | 5 | COLONY | — | 0 | 0 |
| Acinetobacter calcoaceticus anitratus | 5 | COLONY | — | 0 | 0 |
| Branhamella catarrhalis | 63 | COLONY | 63 | 63 | 63 |
| Kingella denitrificans | 3 | COLONY | — | 0 | 0 |
| Kingella indologenes | 2 | COLONY | — | 1 | 1 |
| Moraxella atlantae | 2 | COLONY | — | 0 | 0 |
| Moraxella lacunata | 2 | COLONY | 0 | 0 | 0 |
| Moraxella nonliquefaciens | 5 | COLONY | 0 | 0 | 0 |
| Moraxella osloensis | 5 | COLONY | 0 | 0 | 0 |
| Moraxella phenylpyruvica | 2 | COLONY | 0 | 0 | 0 |
| Moraxella urethralis | 4 | COLONY | 0 | 0 | 0 |
| Neisseria cinerea | 1 | COLONY | 0 | 0 | 0 |
| Neisseria elongata | 2 | COLONY | 0 | 0 | 0 |
| Neisseria flavescens | A | COLONY | 0 | 0 | 0 |
| Neisseria gonorrhoeae | 5 | COLONY | 0 | 0 | 0 |
| Neisseria lactamica | 2 | COLONY | 0 | 0 | 0 |
| Neisseria meningitidis | 5 | COLONY | 0 | 0 | 0 |
| Neisseria mucosa | 2 | COLONY | 0 | 0 | 0 |
| Neissera polysaccharea | 1 | COLONY | — | 0 | 0 |
| Neisseria sicca | 5 | COLONY | 0 | 0 | 0 |
| Neisseria subflava | 2 | COLONY | 0 | 0 | 0 |
| Neisseria subflava (flava) | 2 | COLONY | — | 0 | 0 |
| Neisseria subflava (perflava) | 1 | COLONY | — | 0 | 0 |
| ANIMAL STRAINS | | | | | |
| Neisseria ovis | 1 | COLONY | 0 | 0 | 0 |
| Neisseria caviae | 1 | COLONY | 1 | 1 | 1 |
| Neisseria cuniculi | 1 | COLONY | 0 | 0 | 0 |
| Neisseria animalis | 1 | COLONY | — | 0 | 0 |
| Neisseria canis | 1 | COLONY | — | 1 | 1 |
| HAEMOPHILUS SPP | | | | | |
| Haemophilus influenzae | 5 | COLONY | 0 | 0 | 0 |
| Haemophilus parainfluenzae | 5 | COLONY | — | 0 | 0 |
| Haemophilus haemolyticus | 5 | COLONY | — | 0 | 0 |
| Haemophilus parahaemolyticus | 5 | COLONY | — | 0 | 0 |
| Haemophilus aphrophilus | 2 | COLONY | — | 0 | 0 |
| Haemophilus paraphrophilus | 5 | COLONY | — | 0 | 0 |

TABLE 1-continued
RESULTS OF HYBRIDIZATION EXPERIMENTS

| MICROORGANISM | No STRAINS TESTED | PROBE TEST METHOD | No STRAINS THAT HYBRIDIZE WITH | | |
|---|---|---|---|---|---|
| | | | 550 BP | 150 BP | 400 BP |
| *Haemophilus segnis* | 5 | COLONY | — | 0 | 0 |
| AEROBIC, GRAM + | | | | | |
| *Corynebacterium xerosis* | 1 | DOT BLOT | — | 0 | 0 |
| *Micrococcus lysodisticus* | 1 | DOT BLOT | — | 0 | 0 |
| *Staphylococcus aureus* | 1 | DOT BLOT | — | 0 | 0 |
| *Streptococcus pneumoniae* | 1 | DOT BLOT | — | 0 | 0 |
| *Streptococcus viridans* | 1 | DOT BLOT | — | 1 | 0 |
| *Streptococcus salivarius* | 1 | DOT BLOT | — | 0 | 0 |
| *Streptococcus a-hemolytic* | 1 | DOT BLOT | — | 1 | 0 |
| *Streptococcus pyogenes* | 1 | DOT BLOT | — | 0 | 0 |
| AEROBIC, GRAM − | | | | | |
| *Enterobacter cloacae* | 1 | COLONY | — | 0 | 0 |
| *Escherichia coli* | A | COLONY | 0 | 0 | 0 |
| *Klebsiella pneumoniae* | 1 | COLONY | — | 0 | 0 |
| *Proteus mirabilis* | 1 | COLONY | — | 0 | 0 |
| *Pseudomonas aeruginosa* | 1 | COLONY | — | 0 | 0 |
| *Pseudomonas putida* | 1 | COLONY | — | 0 | 0 |
| *Salmonella* spp (group B) | 1 | COLONY | — | 0 | 0 |
| *Seratia marcescens* | 1 | COLONY | — | 0 | 0 |
| *Shigella* spp. | 1 | COLONY | — | 0 | 0 |
| ANAEROBIC, GRAM + | | | | | |
| *Actinomyces israelii* | 1 | DOT BLOT | — | 0 | 0 |
| *Eubacterium limosum* | 1 | DOT BLOT | — | 0 | 0 |
| *Lactobacillus* spp | 1 | DOT BLOT | — | 0 | 0 |
| *Peptostreptococcus assacharolyticus* | 1 | DOT BLOT | — | 0 | 0 |
| *Propionibacterium acnes* | 1 | DOT BLOT | — | 0 | 0 |
| ANAEROBIC, GRAM − | | | | | |
| *Bacteroides fragilis* | 1 | DOT BLOT | — | 0 | 0 |
| *Bacteroides melaninogenicus* | 1 | DOT BLOT | — | 0 | 0 |
| *Fusobacterium nucleatum* | 1 | DOT BLOT | — | 0 | 0 |
| *Veillonella parvula* | 1 | DOT BLOT | — | 0 | 0 |

—: not tested

The 150 bp probe hybridized to *B. catarrhalis* and to *S. viridans* and *Streptococcus a*-hemolytic, but the 400 bp probe will only hybridize with *B. catarrhalis* DNA and with one *Neisseria caviae* strain, which is a non-human strain. There is also slight hybridization with one out of two *K. indologenes* strains but according to Lennette et al (the Manual of Clinical Microbiology, published by the American Society for Microbiology) this bacterium is seldom encountered in clinical samples and has only been isolated from infected eyes, where *B. catarrhalis* is never found.

EXAMPLE 1

(1) Differential hybridization: *B. catarrhalis* chromosomal DNA, preferably ATCC 53879 DNA and *H. influenzae* chromosomal DNA were digested with a restriction enzyme, preferably AseI, for 3 hours at 37° C. and the resulting digestions were electrophoresed on a 0.7% agarose gel at 30 volts overnight. The DNA on the gel was then Southern transferred onto a solid support, preferably a nylon membrane according to Maniatis et al. (Molecular Cloning: A Laboratory Manual, 1982, Cold Spring Harbor, N.Y.). This membrane was then baked overnight at 65° C. or for 2 hours under vacuum at 80° C. to irreversibly fix the DNA and was subjected to a hybridization with a $^{32}$P labeled *B. catarrhalis* ATCC 53879 chromosomal DNA probe. The conditions for pre-hybridization, hybridization and post hybridization washes are as described in the detailed description. The detection of hybridized probe was done by exposing the membrane to an X-ray film (autoradiography). After development of the film, a region of *B. catarrhalis* chromosomal fragments to which there was no corresponding hybridization with *H. influenzae* DNA was identified. (2) Isolation and cloning of fragments: These fragments then had to be isolated and purified to be subsequently cloned and tried as probes. To do this, a large quantity of *B. catarrhalis* ATCC 53879 chromosomal DNA was digested with AseI restriction endonuclease and run on a preparative 0.6% low melting point agarose gel. The fragments of interest were cut out of the gel, purified according to Maniatis et al. and cloned into dephosphorylated AseI digested pBR322. The ligation mixture was transformed into *E. coli* HB101 by the method of Chung and Miller (1988, Nucleic Acids Research. 16:3580.), or the $CaCl_2$ method of Maniatis et al. and plated on selective media, in this case, tetracycline plates. (3) Selection of strong clones: The colonies that grew on these plates were tested for ampicillin inactivation; the recombinant clones were subjected to Birnboim and Doly (Nucleic Acids Research, 7:1513–1523) mini-preparations of plasmid DNA. These plasmid preparations were then electrophoresed on 0.7% agarose gels; the gels submitted to a Southern transfer and the membrane subsequently hybridized to a *B. catarrhalis* ATCC 53879 chromosomal DNA probe. (4) Isolation of probe fragment: Once a clone is selected, its plasmid DNA is isolated in large quantities and purified on Cesium Chloride-Ethidium Bromide density gradients. The inserted fragment of chromosomal DNA is then separated from the pBR322 vector by digestion with AseI and subsequent purification on low melting point agarose gel. This purified fragment is then ready for testing as a probe. (5) Labeling of the probe: The label used is $\alpha$-$^{32}$P(dATP), a radioactive nucleotide that can be incorporated enzymatically into a double stranded DNA molecule. The fragment of interest is first rendered single stranded by heating at 95° C. for 5 minutes, then a random primer mix is allowed to anneal to the strands of the fragments. These primers, once annealed provide a staring point for synthesis of DNA. DNA polymerase, usually the Klenow fragment, is provided along with the 4 nucleotides, one of which is radioactive. When the reaction is terminated, the mixture of new DNA molecules is once again denatured to provide radioactive single stranded DNA molecules i.e. the probe. (6) Colony hybridizations: All the strains that have to be tested against the probe are inoculated onto a nylon membrane sitting in a petri dish, each strain being assigned a number. The bacteria are allowed to grow for 3 to 5 hours, and are then lysed in the following manner: The nylon membrane is treated with 4 solutions successively; 3M paper disks are flooded with these solutions and the membranes are then laid on these filter papers for varying times. The first treatment is with a 10% solution of SDS for 3 minutes, the second is 0.5M NaOH, 0.5M Tris pH 8.0 for 5 minutes, the third is 0.5M NaCl, 0.5M Tris pH 8.0 for 5 minutes, and the fourth is 2×SSC (see detailed description for composition of SSC) for 5 minutes. After this treatment, the cells are lysed and the DNA is denatured; the next step is the fixation of the DNA on the membrane by baking at 65° C. overnight. The hybridization is done as described above and in the detailed description. After autoradiography, the specificity of the probe can be determined.

EXAMPLE 2

Same as example 1 except that the label is non radioactive. In this case the detection method depends on the label used.

EXAMPLE 3

Same as example 1 except that testing of the strains is done by a dot blot assay instead of a colony hybridization assay. The dot blot assay requires that total DNA be isolated from each strain to be tested beforehand. The whole cell DNA solutions are deposited on a nylon membrane via a dot blot apparatus (Bio Rad ®), washed and denatured before being irreversibly fixed by baking.

EXAMPLE 4

Same as example 1 except that fragments are purified by electroelution instead of low melting point agarose. This method implies eluting the DNA out of an agarose band and into a small volume of buffer by passing a current though the band.

EXAMPLE 5

Same as example 1 except that the vector used for the cloning can be any vector that contains an AseI site that inactives a resistance gene, or provides another seletion method such as non production of β-galactosidase. The selective media are according to the vector chosen.

We claim:

1. A method for detecting the presence of *Branhamella catarrhalis*, said method comprising:
   (a) depositing and fixing on an inert support a sample containing DNA fragments in substantially single stranded form;
   (b) contacting said fixed single-stranded genetic material with a labelled probe comprising a fragment of *B. catarrhalis* chromosomal DNA, said fragment containing at one end an AseI restriction endonuclease site and at the opposite end a PstI restriction endonuclease site, said fragment including an NdeI site at about 0.1 kbp from said AseI site and being about 0.4 kbp in length and 0.26 Mdal in molecular weight and being obtained by digesting *B. catarrhalis* chromosomal DNA with restriction endonuclease AseI, cloning said AseI-AseI fragment into a suitable vector, selecting a recombinant plasmid containing an inserted fragment of about 0.55 kbp of *B. catarrhalis* chromosomal DNA having an NdeI site and digesting said recombinant plasmid with restriction endonucleases AseI and PstI, under conditions such that said AseI-PstI fragment can hybridize with *B. catarrhalis* DNA in said sample whereby a complex is formed; and
   (c) detecting duplex formation on said support by means of said label.

2. The method of claim 1, wherein said label being either radioactive or non-radioactive.

* * * * *